US011684253B2

(12) United States Patent
Mao et al.

(10) Patent No.: US 11,684,253 B2
(45) Date of Patent: Jun. 27, 2023

(54) 2D MULTI-LAYER THICKNESS MEASUREMENT WITH RECONSTRUCTED SPECTRUM

(71) Applicant: TOPCON CORPORATION, Tokyo (JP)

(72) Inventors: Zaixing Mao, Tokyo (JP); Zhenguo Wang, Ridgewood, NJ (US); Bin Cao, Wayne, NJ (US); Kinpui Chan, Ridgewood, NJ (US)

(73) Assignee: TOPCON CORPORATION, Tokyo (JP)

( * ) Notice: Subject to any disclaimer, the term of this patent is extended or adjusted under 35 U.S.C. 154(b) by 396 days.

(21) Appl. No.: 16/855,393

(22) Filed: Apr. 22, 2020

(65) Prior Publication Data

US 2020/0337553 A1 Oct. 29, 2020

Related U.S. Application Data

(60) Provisional application No. 62/837,785, filed on Apr. 24, 2019.

(51) Int. Cl.
| | | |
|---|---|---|
| *G01J 3/45* | (2006.01) | |
| *A61B 3/10* | (2006.01) | |
| *A61B 3/00* | (2006.01) | |
| *A61B 3/14* | (2006.01) | |
| *G01B 9/02* | (2022.01) | |
| *G01B 11/06* | (2006.01) | |

(52) U.S. Cl.
CPC ............ *A61B 3/101* (2013.01); *A61B 3/0025* (2013.01); *A61B 3/14* (2013.01); *G01B 9/02041* (2013.01); *G01B 9/02083* (2013.01); *G01B 11/06* (2013.01); *G01J 3/45* (2013.01)

(58) Field of Classification Search
CPC ......... A61B 3/101; A61B 3/0025; A61B 3/14; G01B 9/02041; G01B 9/02083; G01B 11/06; G01B 11/0625; G01B 11/0633; G01J 3/45
See application file for complete search history.

(56) References Cited

U.S. PATENT DOCUMENTS

2016/0338585 A1* 11/2016 Arieli .................. A61B 3/0025
2017/0299432 A1* 10/2017 Watanabe ................ G01J 3/45

FOREIGN PATENT DOCUMENTS

| EP | 3520680 A1 | 8/2019 |
|---|---|---|
| WO | 2015132788 A2 | 9/2015 |

OTHER PUBLICATIONS

Paoletti, et al., "A new deep convolutional neural network for fast hyperspectral image classification", ISPRS Journal of Photogrammetry and Remote Sensing, vol. 145, 2017, pp. 120-147.

(Continued)

*Primary Examiner* — Jonathan M Hansen
(74) *Attorney, Agent, or Firm* — Pearne & Gordon LLP

(57) ABSTRACT

A method for determining thickness of layers of the tear film includes reconstructing a full- or hyper-spectral interference pattern from an imaged multi-spectral pattern. Tear film thickness can then be estimated from the full- or hyper-spectral interference pattern. Using a full- or hyper-spectral interference pattern provides a greater number of frequency sampling points for increased tear film thickness estimation accuracy, without traditional time consuming techniques.

12 Claims, 5 Drawing Sheets

(56) References Cited

OTHER PUBLICATIONS

Alvarez-Gila, et al., "Adversarial Networks for Spatial Context-Aware Spectral Image Reconstruction from RGB", arXiv:1709.00265v2 [cs.CV], Mar. 14, 2018, pp. 1-13.
Nie, et al., "Deeply Learned Filter Response Functions for Hyperspectral Reconstruction", Computer Vision Foundation (CVF), In Proceedings of the IEEE Conference on Computer Vision and Pattern Recognition, DOI: 10.1109/CVPR.2018.00501, Oct. 2018, pp. 4767-4776.
Galliani, et al., "Learned Spectral Super-Resolution", arXiv:1703.09470v1 [cs.CV], Mar. 28, 2017. pp. 1-10.
Choi, et al., "High-Quality Hyperspectral Reconstruction Using a Spectral Prior", ACM Transactions on Graphics (TOG), vol. 36, No. 6, Article 218, Nov. 2017, pp. 218:1-218:13.
Extended European Search Report for European Application No. 20171246.0 dated Sep. 23, 2020.
King-Smith et al., "Tear Film Interferometry and Corneal Surface Roughness", Investigative Ophthalmology & Visual Science, Association for Rearch in Vision and Ophthalmology, US, vol. 55, No. 4, Mar. 31, 2014, pp. 2614-2618, XP009522899, ISSN: 0146-0404, DOI:10.1167/IVOS.14-14076.
Tremmel, et al., "Inline hyperspectral thickness determination of thin films using neural networks", Proceedings of SPIE; [Proceedings of SPIE ISSN 0277-786X vol. 10524], SPIE, US, vol. 10213, Apr. 28, 2017, pp. 102130G-102130G, XP060089950, DO1: 10.1117/12.2262070.

\* cited by examiner

2D MULTI-LAYER THICKNESS MEASUREMENT WITH RECONSTRUCTED SPECTRUM

CROSS REFERENCE TO RELATED APPLICATIONS

This application claims priority to U.S. Provisional Application No. 62/837,785, filed on Apr. 24, 2019, entitled "2D MULTI-LAYER THICKNESS MEASUREMENT WITH RECONSTRUCTED SPRECTRUM", the entirety of which is incorporated herein by reference.

BACKGROUND OF THE INVENTION

Dry eye has become one of the most common causes for ophthalmological doctor visits. Dry eye is a multifactorial disease of the ocular surface that is related to the tear film. One method to diagnosing dry eye is to assess the quantity of tears by measuring the thickness of the tear film. As illustrated in FIG. 1, the tear film 100 comprises the outer layers of the eye including a lipid layer 102 that is about 50 nm thick, and a muco-aqueous layer 104 (also referred to as a mucous and/or aqueous layer) that is collectively about 1.5 µm thick. The eye further includes the cornea 106 following the muco-aqueous layer, which is about 0.5 mm thick. Currently, few technologies exist for accurately and efficiently imaging and analyzing the layers of the tear film 100 (e.g., determining layer thickness), for example, to objectively assist dry eye diagnosis.

Interferometric techniques are among the currently available non-invasive measurements. Of these, one approach relies on a correlation between an image color and the lipid layer thickness, either quantitatively or qualitatively. Theoretically, the analysis is performed based on two-dimensional (2D) images, while typically only the average thickness within a fairly large area is presented. However, this approach is usually limited for relative lipid layer thickness estimates, and may be susceptible to phase ambiguity and uncertainty when performing absolute thickness measurements.

BRIEF SUMMARY OF THE INVENTION

According to a first example of the present disclosure, a method for measuring layer thickness of a structure comprises: acquiring a multi-spectral interference pattern of the structure; performing a hyperspectral reconstruction on the multi-spectral interference pattern, thereby generating a reconstructed full- or hyper-spectral interference pattern; and estimating the layer thickness based on the reconstructed full- or hyper-spectral interference pattern.

According to another example of the present disclosure, a method for measuring layer thickness of a structure comprises: acquiring a full- or hyper-spectral interference pattern of the structure with a hyperspectral camera; and estimating the layer thickness based on the hyperspectral interference pattern.

In various embodiments of the above examples, the structure is a tear film of an eye; the multi-spectral interference pattern is acquired by capturing a reflected light from the structure with an RGB camera; the multi-spectral interference pattern is acquired by capturing a reflected light from the structure with a dual color camera; the multi-spectral interference pattern is acquired by capturing a reflected light from the structure with a narrow-band multi-spectral camera; the hyperspectral reconstruction on the multi-spectral interference pattern is performed by a machine learning system trained to output the full- or hyper-spectral interference pattern based on an input multi-spectral interference pattern; the layer thickness is estimated by comparing the full- or hyper-spectral interference pattern with a look-up table; the layer thickness is estimated by performing a curve-fitting to the full- or hyper-spectral interference pattern; the layer thickness is estimated by supplying the full- or hyper-spectral interference pattern to a machine learning system trained to output a layer thickness based on the input full- or hyper-spectral interference pattern; the method further comprises displaying the estimated layer thickness; the acquired multi-spectral interference pattern is out of focus, and the method further comprises focusing the out-of-focus multi-spectral interference pattern prior to performing the hyperspectral reconstruction; and/or the focusing is performed by a machine learning system trained to output an in-focus multi-spectral interference pattern based on an input out-of-focus multi-spectral interference pattern.

DETAILED DESCRIPTION OF THE INVENTION

Figure 1:
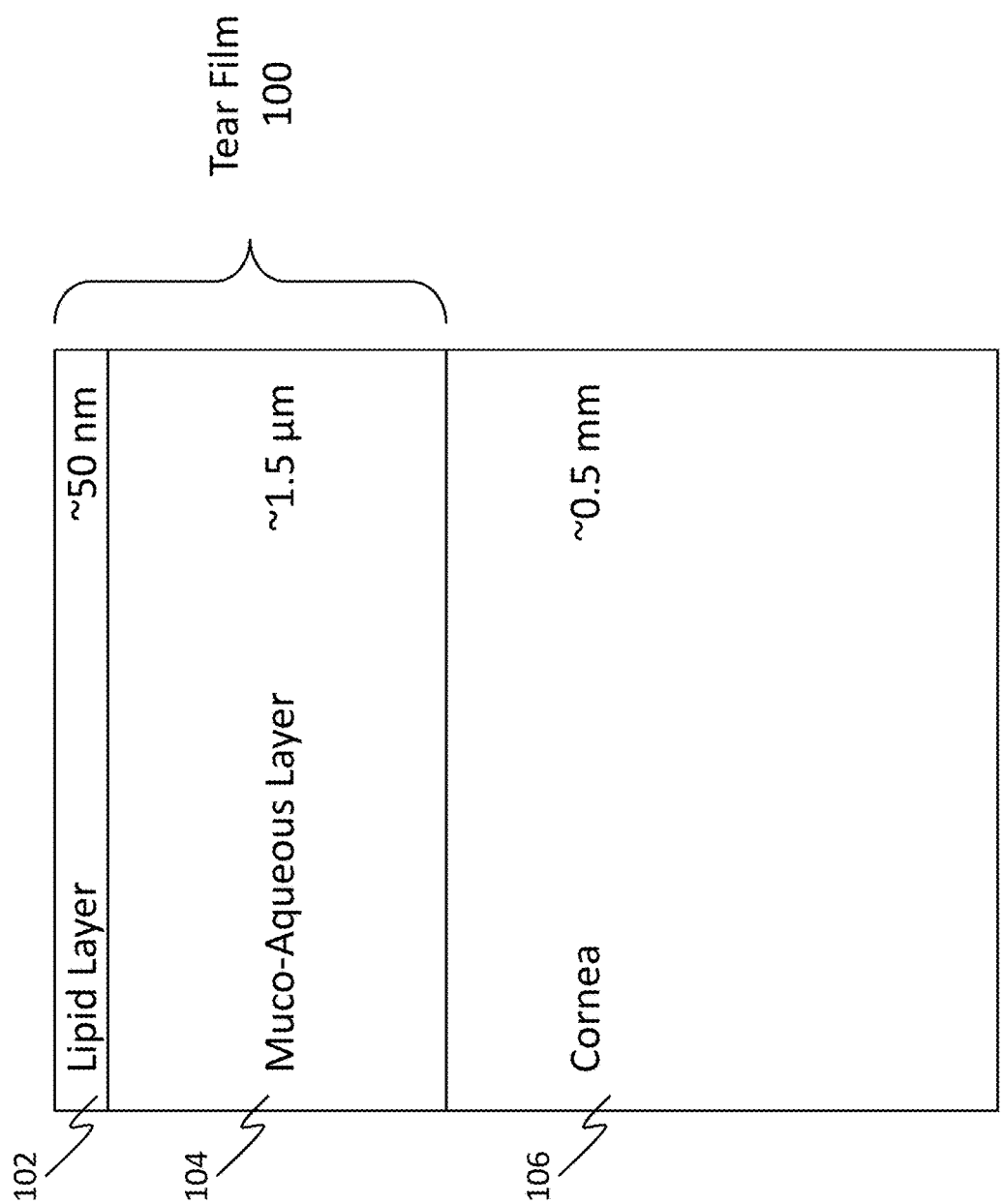
FIG. 1 schematically illustrates the tear film and cornea.

As presented herein, interferometry may be used to measure layer thicknesses of an object by imaging the object with multiple spectral bands. For example, in some embodiments, a plurality of spectral bands (and in particular, "narrow bands," which have a narrower spectral bandwidth than conventional RGB imaging) may be used to provide a sufficient signal strength for 2D layer thickness measurement. Further, narrow spectral bandwidths can be used to help enhance the imaging contrast, particularly for muco-aqueous layer measurement. In some embodiments, these multi-spectral bands may be non-overlapping bands or overlapping bands from a RGB camera. Tear film thickness at each imaged location can then be estimated with look-up-table, curve-fitting, or machine learning methods, based on a full- or hyper-spectral interference pattern reconstructed from the imaged spectral patterns.

The number of spectral bands can affect the accuracy and applications of such imaging. Using a relatively larger number of spectral bands can increase accuracy, but is time consuming and thus can limit the ability to measure dynamic objects such as the tear film. On the other hand, a relatively fewer number of spectral bands can allow live-speed measurement, but may not provide sufficient information for accurate curve-fitting. Hyperspectral reconstruction of the spectral bands allows for increased accuracy with a decreased number of spectral bands by reconstructing a full- or hyper-spectrum response from limited spectrum band measurements. In other words, the hyper-spectral reconstruction produces an interference pattern similar to one that might have been captured with a full-spectrum camera (and thus having the associated benefits of additional data points yielding increased thickness estimation accuracy), while maintaining the benefits of multi-spectral imaging.

It should be appreciated that as used herein, the term "full spectrum" refers to a continuous spectral distribution, "hyper-spectral" typically refers to at least 100 discrete spectral bands, and "multi-spectral" typically refers to about 20 discrete spectral bands. In many instances, the prefixes 'full' and 'hyper' are used interchangeably to generically refer to spectral reconstructions across many frequencies and bandwidths. Further, it is noted that multi-spectral signals may have more or less than 20 discrete spectral bands, and hyper-spectral signals may have more or less than 100 discrete spectral bands, so long as the hyper-spectral signals have more discrete spectral bands than the multi-spectral signals.

While some have attempted to perform hyperspectral reconstruction with machine learning, those attempts have been to determine reflectance (e.g., of a household object) and do not relate to inference patterns of a multi-layered structure (e.g., the tear film). Moreover, most attempts have focused on the reconstruction of images from RGB cameras, rather than cameras capturing a series of narrow spectral bands.

Figure 2:
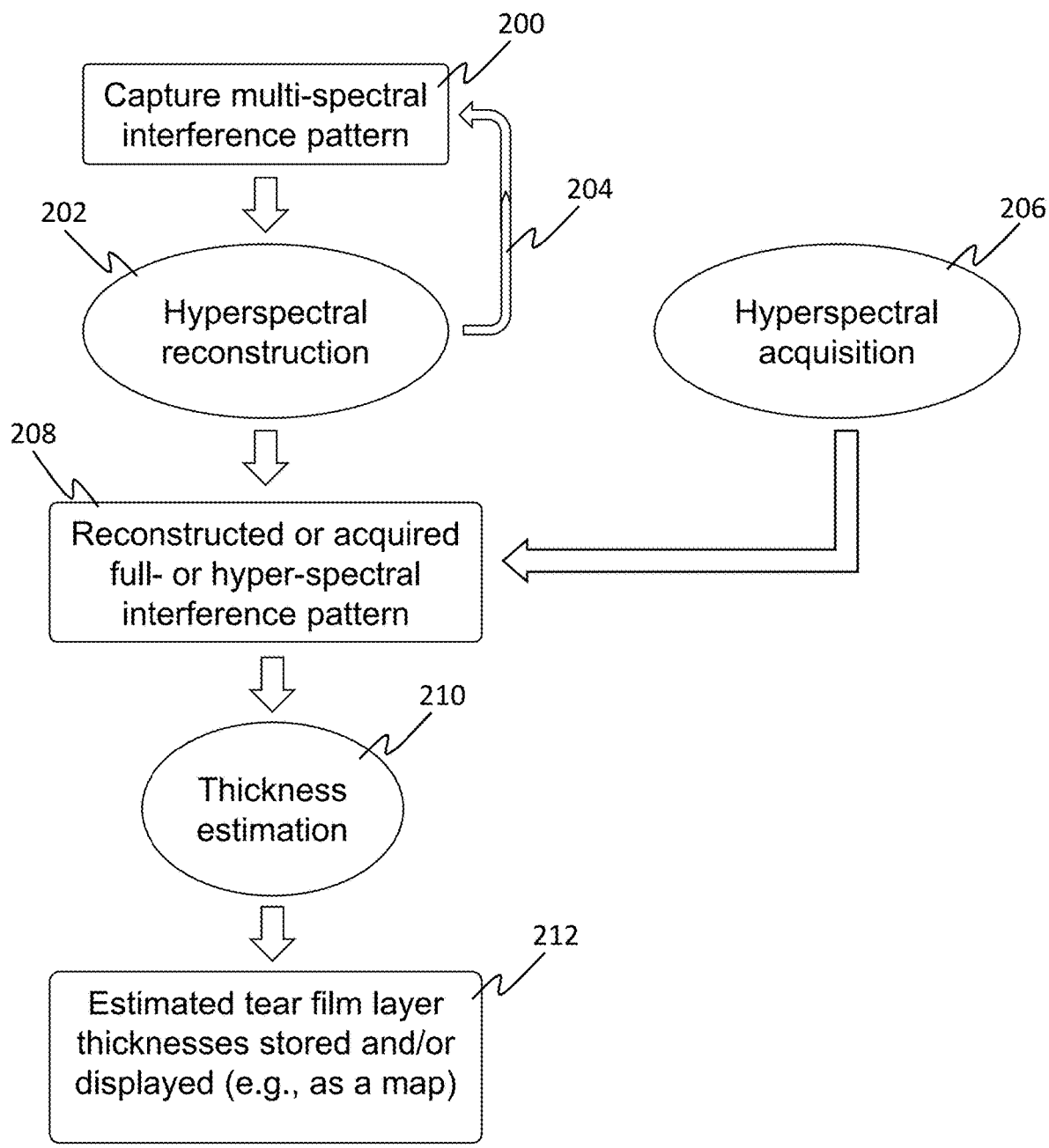
FIG. 2 illustrates an example thickness estimation method of the present disclosure that uses hyper-spectral reconstruction of multi-spectral band images.

FIG. 2 illustrates an overview of the method described herein related to the above hyperspectral reconstruction of multi-spectral band imaging. As seen therein, first, a multi-spectral band interference pattern (that could be used to, for example, form an image) is captured 200 for each location in a region of interest of a structure (e.g., the tear film of an eye) for which the layer thickness is to be measured. The interference pattern may be captured locally just before performing the subsequent thickness measurement processing, or may have been captured remotely at an earlier point in time. If captured earlier, the interference pattern may be stored and acquired from storage to perform the subsequent processing. The spectral bands used for imaging may be a dual-color spectrum, an RGB spectrum, a plurality of narrow spectral bands, or a plurality of user-selected spectral bands. The particular spectral bands to be captured may be determined by a machine learning system trained to determine the optimum spectral bands for a desired imaging object or result.

A hyperspectral reconstruction 202 of the captured multi-spectral interference pattern is then performed to produce a reconstructed full- or hyper-spectral interference pattern 208. The hyper-spectral reconstruction 202 can be performed by techniques such as compressed sensing. With compressed sensing, the signal can be reconstructed through a series of optimizations as long as: 1) the signal is sparsely distributed in some space; and 2) there is random sampling. The present disclosure satisfies these conditions because, respectively: 1) there are only two unknown thicknesses, and 2) the multi-spectral bands can be randomly chosen instead of having them uniformly distributed.

The hyper-spectral reconstruction 202 can also be performed by machine learning techniques. In these embodiments, a hyperspectral reconstruction machine learning system may be supervise-trained using pairs of multi-spectral and hyper-spectral images of the same object. During training, the difference between the hyper-spectral image and the reconstructed hyper-spectral image from the machine learning system is reduced by adjusting the parameters in the machine learning system. Accordingly, the machine learning system learns the parameters that properly reconstruct a hyper-spectral image 208 from given multi-spectral inputs.

The hyperspectral reconstruction 202 may also be aided by a feedback loop 204 that can be referenced to identify an optimal set of multi-spectral bands as part of a learning process. For example, a quality of the hyper-spectral reconstruction 202 can be fed back to determine which spectral bands of an acquired multi-spectral interference pattern yield the highest accuracy for tear film thickness interference pattern reconstruction 202. This feedback 204 can be applied to either conventional or machine learning-based hyper-spectral reconstruction techniques during development of the desired reconstruction method.

In still other embodiments, a hyper-spectral camera may be used to obtain 206 the full- or hyper-spectral interference pattern 208 directly without requiring reconstruction from a multi-spectral interference pattern as noted above.

A thickness estimation technique 210 is then performed on the full- or hyper-spectral interference pattern (either as reconstructed or obtained directly) 208. The thickness estimation may be of any or all of the layers of a multi-layer object, and/or of the total thickness of the object. As noted above, the thickness estimation may be performed by using a look-up table (e.g., comparing detected signal intensities at particular spectral band wavelengths to known corresponding thicknesses), curve fitting techniques, machine learning techniques, Fourier transform techniques, and the like. Such Fourier transform techniques may be those described in U.S. patent application Ser. No. 16/829,673, filed on Mar. 25, 2020 and entitled "METHOD AND APPARATUS FOR MEASURING TEAR FILM THICKNESS USING OPTICAL INTERFERENCE", which is herein incorporated by reference in its entirety. Other techniques such as those described in U.S. patent application Ser. No. 16/252,818, filed on Jan. 21, 2019 and published on Aug. 1, 2019 as US Publication No. 2019/0231187, and entitled "2D MULTI-LAYER THICKNESS MEASUREMENT", which is herein incorporated by reference in its entirety.

For example, if an interference pattern has known values $\{x\}$, and an unknown target layer thickness is y, the thickness estimation technique can associate the values $\{x\}$ and y. When using a look-up table, the spectral interference patterns of different thickness combinations are simulated (e.g., using a tear film physics model), and stored in a table. During thickness estimation, the interference pattern values $\{x\}$ are used as a key to search the table to find the best matching interference pattern stored in the table. The corresponding thickness(es) in the table is then considered as the target tear film layer thickness(es) for the measured interference pattern.

When using a curve fitting technique, the interference pattern values $\{x\}$ are directly used to fit the tear film physics model (or like model) having two unknown values (corresponding to the unknown layer thicknesses). The fitted model yields the tear film layer thicknesses by determining the variable values for which the model best fits the interference pattern values $\{x\}$.

When using machine learning, a pre-trained machine learning system is used to estimate the thicknesses from an input of interference pattern values $\{x\}$. During supervised training, the system is presented with pairs of interference patterns and their corresponding tear film layer thicknesses. This training data may be generated from simulations (e.g., from tear film physics models) or from captured real samples. As training occurs, the machine learning system learns to correctly predict the tear film thicknesses based on input interference patterns.

Finally, the determined layer thickness(es) may be stored for later analysis or displayed directly or as a thickness map 212. The thickness map may be a 2D image of the imaged object, where each pixel corresponds to an imaged location and has an intensity, color, brightness, or the like corresponding to the determined thickness at that location. In other embodiments, the thickness map may be a 3D map illustrating the thickness at each 2D location via the third dimension.

Figure 3:
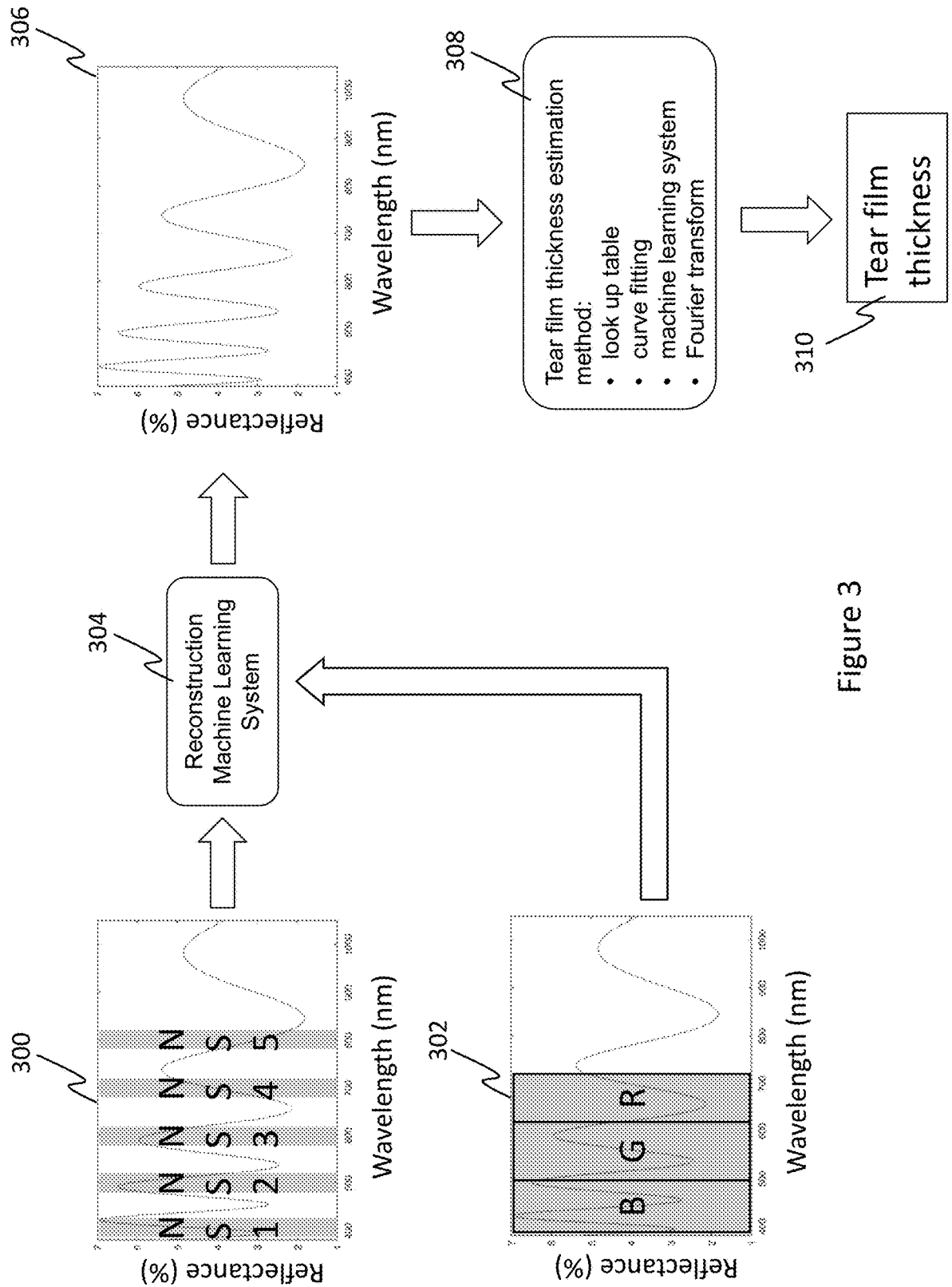
FIG. 3 graphically illustrates the method of FIG. 2.

FIG. 3 graphically illustrates the method of FIG. 2. As seen therein, a hyper-spectral interference pattern 306 is formed by capturing interference data multiple spectral bands. In one example 300, the multiple spectra may comprise five narrow spectral bands of about 40 nm each, and centered at 400, 500, 600, 700, and 800 nm. In another example the bands may be between about: 425-475 nm, 500-550 nm, 650-700 nm, 750-800 nm, and 950-1000 nm. In still another example 302, the spectral bands may correspond to red, green, and blue bands of an RGB or dual color camera. As noted above, however, any number of bands of different bandwidths may be used, and those bands may be chosen by any number of techniques. For example, preferred bands may be identified as discussed above during hyper-spectral reconstruction training, via feedback 204, or by machine learning techniques.

When reconstructing the full- or hyper-spectrum with a machine learning system 304, the acquired multi-spectral interference pattern 300, 302 is input to a machine learning system trained to output a reconstructed full- or hyper-spectrum 306 based on the input multi-spectral pattern 300, 302. As noted above, this reconstruction may also be performed by other techniques and is not limited to machine learning shown in the example of FIG. 3. By reconstructing the full- or hyper-spectrum, a greater number of frequency sampling points are available for later tear film thickness estimation.

The reconstructed spectrum 306 is next analyzed with a thickness estimation technique 308 to determine a tear film thickness 310 at the location corresponding to the full- or hyper-spectrum 306. As noted above, this analysis may occur by comparing the spectrum to a look-up table that relates spectra to thicknesses, a curve fitting technique, or by inputting the reconstructed spectrum into a machine learning system trained to output a thickness based on the input spectrum, or with Fourier transform methods.

Figure 4:
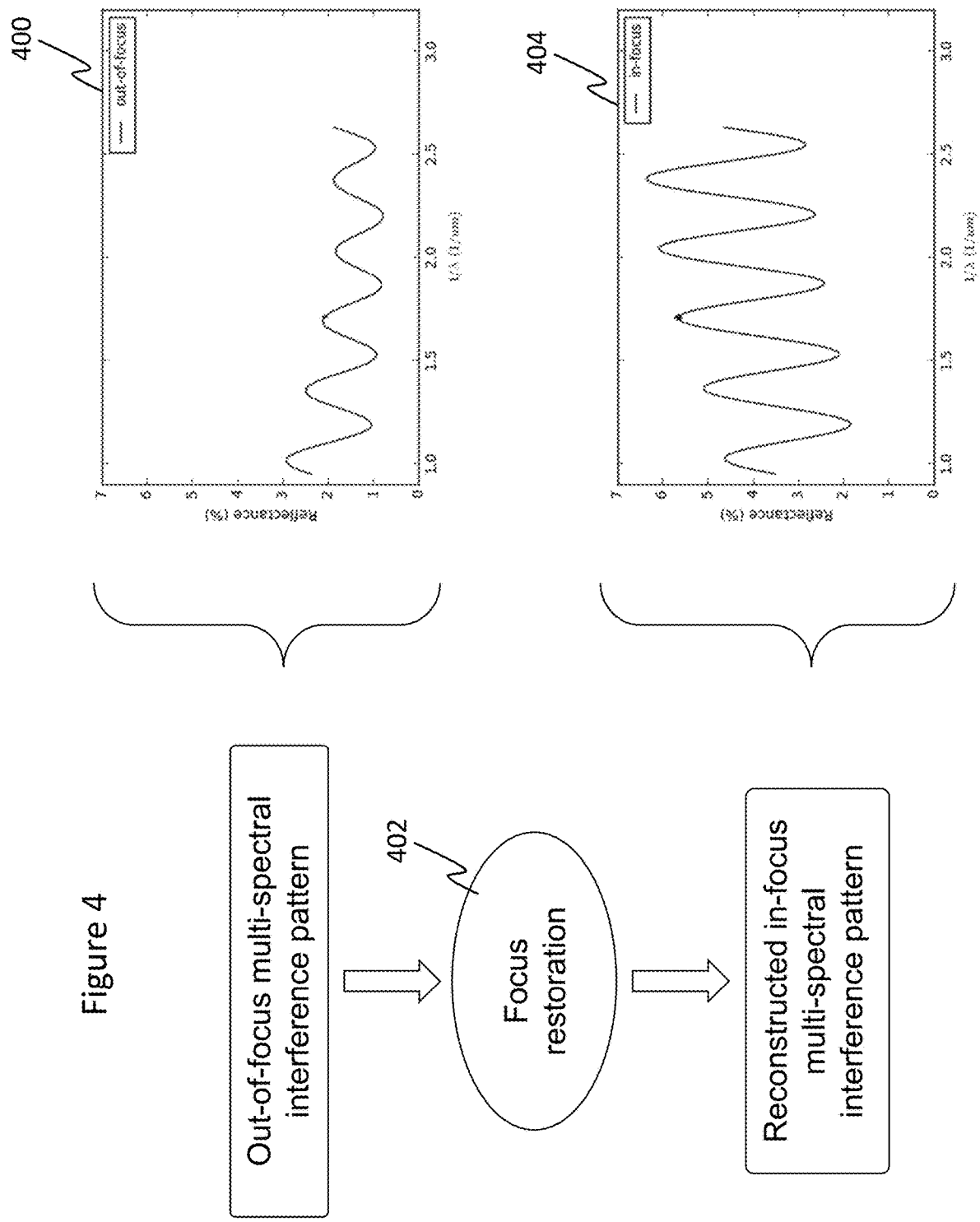
FIG. 4 illustrates pre-processing to re-focus a multi-spectral interference pattern.

In addition to the above, prior to performing a full- or hyper-spectral reconstruction on a multi-spectral interference pattern, the multi-spectral interference pattern may be pre-processed, for example, to remove noise, re-focus the pattern, and the like. Such pre-processing may be independent of the reconstruction. FIG. 4 illustrates an example out-of-focus multi-spectral interference pattern 400 that is input to a focus restoration method 402 to reconstruct the multi-spectral interference pattern in-focus 404. The focus restoration method 402 may be a machine learning system trained to associate out-of-focus patterns with properly in-focus patterns. Thus, the system 402 can output an in-focus pattern from an out-of-focus pattern input to the machine learning system 402. The machine learning system 402 can also generate focus related information captured from different image modalities (e.g., an RGB camera or time-of-flight system) to measure the distance between the camera and the cornea. This information can further help the machine learning system identify an out-of-focus rate, and adjust the out-of-focus interference pattern 500 accordingly to generate the in-focus patterns 404.

Figure 5:
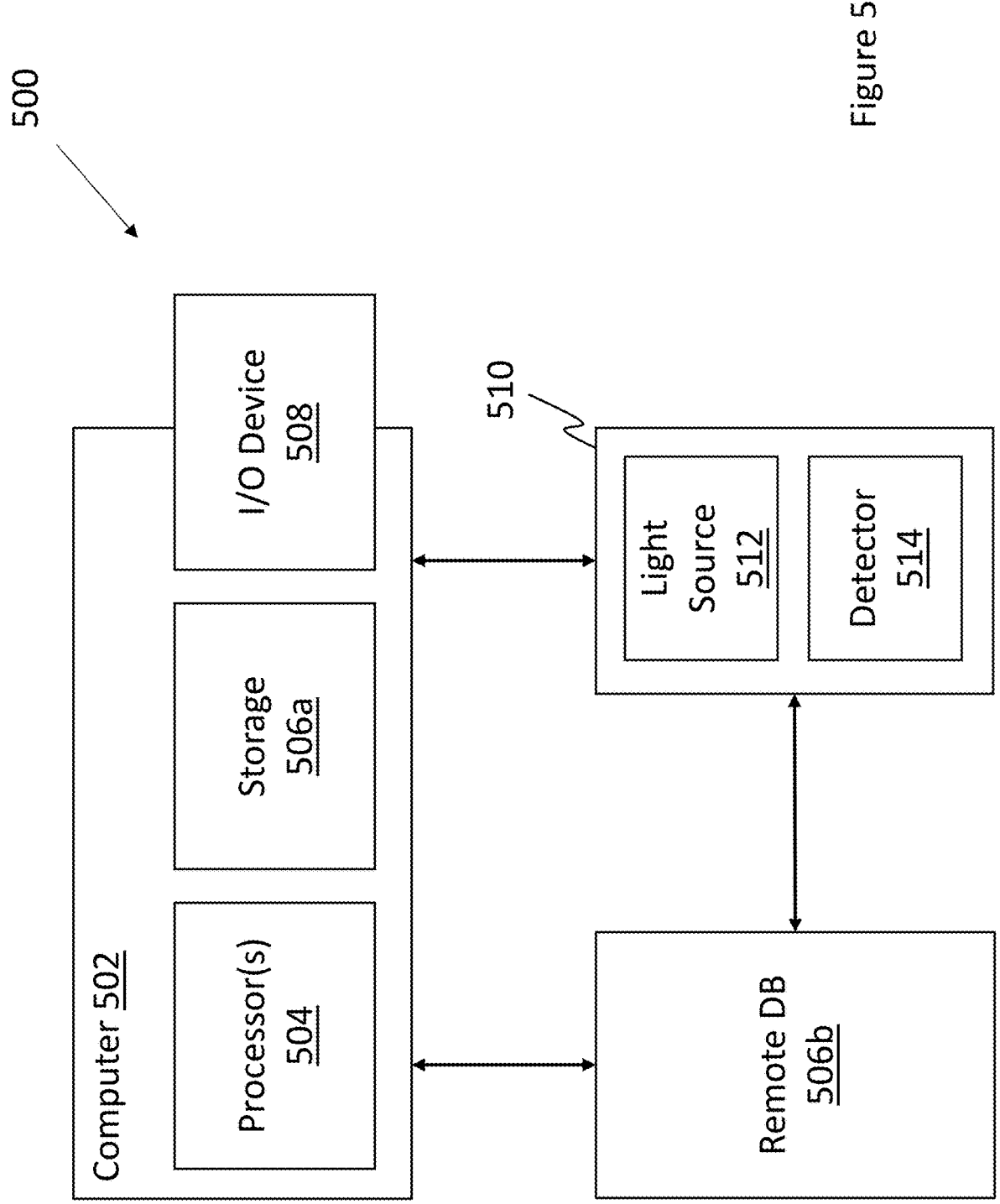
FIG. 5 illustrates an example system for executing the method of the present disclosure.

A system for executing the above-described method is also contemplated within the scope of the present disclosure, and is illustrated in FIG. 5. Such a system 500 may include a computer having one or more processors (e.g., in the form of an integrated circuit(s), discrete circuitry, or the like) 504 for executing the method, storage 506 (such as a hard disk, memory, RAM, or the like) and an input/output interface (e.g., display, keyboard, mouse, and the like) 508. The above-described method may be implemented via software executed by the processor 504 or via hardware (e.g., circuitry, optical filters, or the like). The storage 506 may be located locally 506a with the computer, or remotely, for example at a centralized database 506b. The various above-described machine learning systems may be implemented together in the computer 502 (on one or more of the processors 504), or separately as independent systems.

The system 500 may also be integrated with or separate from imaging system hardware 510 used to capture the interference patterns from the object. For example, the computer 502 may be the same as that used to control an optical coherence tomography system. Where integrated, the system 500 may thus include the imaging system hardware 510 for acquiring the spectral interference patterns discussed above. Such hardware 510 may include, for example, a light source 512 configured to emit light toward an object whose thickness is to be measured; a camera/detector, such as an RGB camera, a dual color camera, a multi-, or full-, or hyper-spectral photodetector/camera (including narrow-band versions thereof) to detect light from the light source 512 that is reflected by the object; and optical elements (e.g., lenses, filters, and the like) configured to supply the light from the light source to the object and supply the reflected light from the object to the cameras and/or photodetectors 514.

While various features are presented above, it should be understood that the features may be used singly or in any combination thereof. Further, it should be understood that variations and modifications may occur to those skilled in the art to which the claimed examples pertain. Similarly, while the above disclosure primarily relates to imaging of the tear film of an eye, the disclosure may also be applied to imaging and determining layer thicknesses for any other multilayer structure.

What is claimed is:

1. A method for measuring layer thickness of a structure comprising:
   acquiring a multi-spectral interference pattern of the structure;
   performing a hyperspectral reconstruction on the multi-spectral interference pattern, thereby generating a reconstructed full- or hyper-spectral interference pattern; and
   estimating the layer thickness based on the reconstructed full- or hyper-spectral interference pattern.

2. The method of claim 1, wherein the structure is a tear film of an eye.

3. The method of claim 1, wherein the multi-spectral interference pattern is acquired by capturing a reflected light from the structure with an RGB camera.

4. The method of claim 1, wherein the multi-spectral interference pattern is acquired by capturing a reflected light from the structure with a dual color camera.

5. The method of claim 1, wherein the multi-spectral interference pattern is acquired by capturing a reflected light from the structure with a narrow-band multi-spectral camera.

6. The method of claim 1, wherein the hyperspectral reconstruction on the multi-spectral interference pattern is performed by a machine learning system trained to output the full- or hyper-spectral interference pattern based on an input multi-spectral interference pattern.

7. The method of claim 1, wherein the layer thickness is estimated by comparing the full- or hyper-spectral interference pattern with a look-up table.

8. The method of claim 1, wherein the layer thickness is estimated by performing a curve-fitting to the full- or hyper-spectral interference pattern.

9. The method of claim 1, wherein the layer thickness is estimated by supplying the full- or hyper-spectral interference pattern to a machine learning system trained to output a layer thickness based on the input full- or hyper-spectral interference pattern.

10. The method of claim 1, further comprising displaying the estimated layer thickness.

11. The method of claim 1, wherein the acquired multi-spectral interference pattern is out of focus, and the method further comprises focusing the out-of-focus multi-spectral interference pattern prior to performing the hyperspectral reconstruction.

12. The method of claim 11, wherein the focusing is performed by a machine learning system trained to output an in-focus multi-spectral interference pattern based on an input out-of-focus multi-spectral interference pattern.

* * * * *